United States Patent
Kim et al.

(10) Patent No.: US 9,710,906 B2
(45) Date of Patent: Jul. 18, 2017

(54) METHOD AND APPARATUS FOR REMOVING DISTORTION BY LIPIDS FROM MAGNETIC RESONANCE IMAGE

(71) Applicants: SAMSUNG ELECTRONICS CO., LTD., Suwon-si (KR); INDUSTRY-ACADEMIC COOPERATION FOUNDATION, YONSEI UNIVERSITY, Seoul (KR)

(72) Inventors: Dong-hyun Kim, Seoul (KR); Joon-sung Lee, Seoul (KR); Min-oh Kim, Seoul (KR); Yoon-ho Nam, Seoul (KR); Eun-hae Joe, Seoul (KR)

(73) Assignees: SAMSUNG ELECTRONICS CO., LTD., Suwon-si (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 467 days.

(21) Appl. No.: 13/845,248

(22) Filed: Mar. 18, 2013

(65) Prior Publication Data
US 2014/0085304 A1    Mar. 27, 2014

(30) Foreign Application Priority Data
Sep. 26, 2012 (KR) .................. 10-2012-0107489

(51) Int. Cl.
*G06K 9/00* (2006.01)
*G06T 7/00* (2017.01)
(Continued)

(52) U.S. Cl.
CPC .......... *G06T 7/0012* (2013.01); *G01R 33/485* (2013.01); *G01R 33/5607* (2013.01); *G06F 19/321* (2013.01)

(58) Field of Classification Search
None
See application file for complete search history.

(56) References Cited

U.S. PATENT DOCUMENTS 4,881,032 A * 11/1989 Bottomley ........... G01R 33/485
                                                                    324/309
5,283,526 A *  2/1994 Spielman ........... G01R 33/4828
                                                                    324/307
(Continued)

FOREIGN PATENT DOCUMENTS

| CN | 1618399 A | 5/2005 |
| CN | 101268380 A | 9/2008 |

(Continued)

OTHER PUBLICATIONS

Schuff et al., "Region Region and Tissue Differences of Metabolites in Normally Aged Brain Using Multislice 1H Magnetic Resonance Spectroscopic Imaging", Magn. Reson. Med., 45, 2001, pp. 899-907.*

(Continued)

*Primary Examiner* — Matthew Bella
*Assistant Examiner* — Jose M Torres
(74) *Attorney, Agent, or Firm* — Sughrue Mion, PLLC

(57) ABSTRACT

A method of removing distortion by lipids from an MR image includes obtaining an MR image including voxels, obtaining data of the voxels from the obtained MR image, estimating a lipid-related spectrum by using the obtained data, and removing the estimated lipid-related spectrum from the obtained data.

28 Claims, 11 Drawing Sheets

(51) Int. Cl.
*G06F 19/00* (2011.01)
*G01R 33/485* (2006.01)
*G01R 33/56* (2006.01)

(56) References Cited

U.S. PATENT DOCUMENTS

| | | | |
|---|---|---|---|
| 5,701,074 A | 12/1997 | Zhu | |
| 5,709,208 A | 1/1998 | Posse et al. | |
| 6,307,368 B1* | 10/2001 | Vasanawala et al. | 324/309 |
| 6,320,381 B1* | 11/2001 | Hennig | 324/312 |
| 6,384,601 B1 | 5/2002 | Wiesler et al. | |
| 7,683,620 B2 | 3/2010 | Lin | |
| 8,054,076 B2 | 11/2011 | Deimling | |
| 8,611,624 B2* | 12/2013 | Poonawalla et al. | 382/128 |
| 2004/0100258 A1 | 5/2004 | Gurr | |
| 2005/0110489 A1 | 5/2005 | Miyoshi | |
| 2005/0122105 A1* | 6/2005 | Avram et al. | 324/314 |
| 2007/0285091 A1* | 12/2007 | Wen et al. | 324/309 |
| 2007/0285094 A1* | 12/2007 | Reeder et al. | 324/313 |
| 2008/0125643 A1* | 5/2008 | Huisman | A61B 5/055 600/420 |
| 2008/0272780 A1 | 11/2008 | Thompson et al. | |
| 2009/0001262 A1* | 1/2009 | Visser | H01J 49/0036 250/282 |
| 2009/0118611 A1* | 5/2009 | He | G01R 33/34046 600/422 |
| 2009/0230960 A1* | 9/2009 | Deimling | A61B 5/055 324/309 |
| 2009/0261823 A1* | 10/2009 | Yu | G01R 33/4828 324/307 |
| 2009/0276187 A1* | 11/2009 | Martin | G01N 24/08 702/189 |
| 2009/0285463 A1 | 11/2009 | Otazo et al. | |
| 2011/0123083 A1* | 5/2011 | Ojha et al. | 382/131 |
| 2011/0144474 A1 | 6/2011 | Ouwerkerk | |
| 2013/0053658 A1* | 2/2013 | Peacock et al. | 600/309 |
| 2014/0064586 A1* | 3/2014 | Peacock, III | G01R 33/4625 382/131 |

FOREIGN PATENT DOCUMENTS

| | | |
|---|---|---|
| CN | 101530324 A | 9/2009 |
| CN | 102124361 A | 7/2011 |
| JP | 5-64635 A | 3/1993 |
| JP | 2001-187038 A | 7/2001 |
| KR | 10-2010-0051200 A | 5/2010 |

OTHER PUBLICATIONS

Soher et al., "Automated Spectral Analysis 111: Application to in Vivo Proton MR Spectroscopy and Spectroscopic Imaging", Magn. Reson. Med., (40)6, 1998, pp. 822-831.*

Haupt et al., "Removal of lipid artifacts in 1H spectroscopic imaging by data extrapolation", Magn. Reson. Med., (35)5, 1996, pp. 378-387.*

Communication dated Oct. 24, 2013, issued by the Korean Intellectual Property Office in corresponding Application No. 10-2012-0107489.

Communication issued Oct. 14, 2015, issued by the State Intellectual Property Office of the People's Republic of China in counterpart Chinese Patent Application No. 201310432072.9.

Communication dated Mar. 26, 2015 issued by the State Intellectual Property Office of P.R. China in counterpart Chinese Patent Application No. 201310432072.9.

Communication dated Apr. 25, 2016, issued by the State Intellectual Property Office of P.R. China in counterpart Chinese Application No. 201310432072.9.

* cited by examiner

FIG. 7A
FIG. 7B
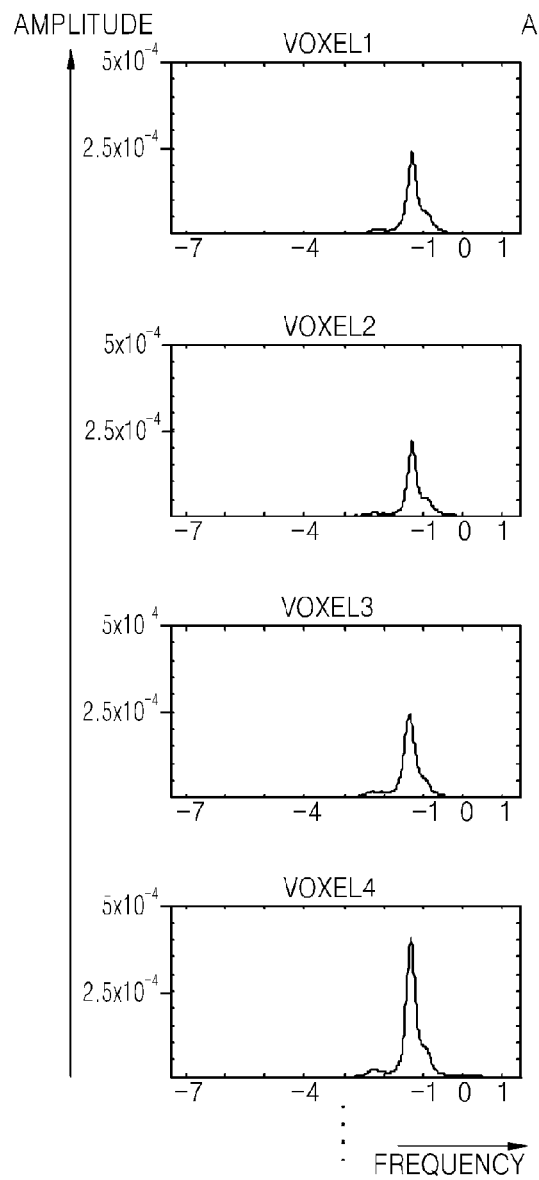
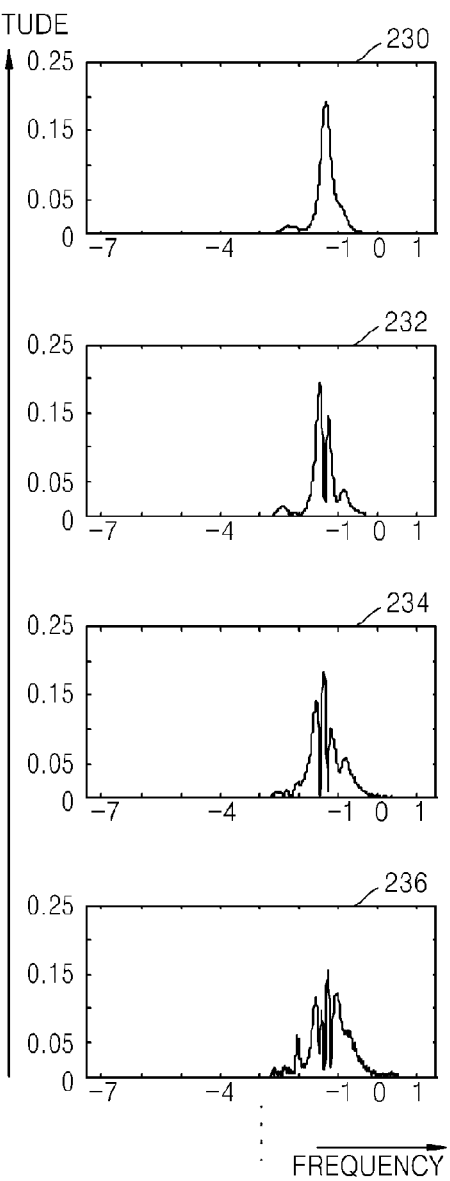

METHOD AND APPARATUS FOR REMOVING DISTORTION BY LIPIDS FROM MAGNETIC RESONANCE IMAGE

CROSS-REFERENCE TO RELATED PATENT APPLICATION

This application claims the benefit of Korean Patent Application No. 10-2012-0107489, filed on Sep. 26, 2012, in the Korean Intellectual Property Office, the disclosure of which is incorporated herein in its entirety by reference.

BACKGROUND

1. Field

Apparatuses and methods consistent with exemplary embodiments relate to removing distortion by lipids from a magnetic resonance (MR) image, and more particularly, to obtaining and removing a spectrum of a lipid component from a spectrum of an MR image.

2. Description of the Related Art

Magnetic resonance spectroscopic imaging (MRSI) is a method of obtaining an image of an object in a non-invasive manner to show a distribution of metabolite of body tissues or biochemical information.

MRSI includes information about a spectrum of metabolite present in each of image voxels. In MRSI, the amount of metabolite of interest is by far smaller than that of moisture or lipids captured by magnetic resonance imaging (MRI). Accordingly, with respect to MRSI, a signal-to-noise ratio (SNR) is low compared to that of a related art MRI method and thus the size of a voxel is relatively large.

In the spectrum information, peaks of metabolite are affected by a chemical shift according to line-broadening and B0 inhomogeneity. Thus, to accurately measure an amount of metabolite in a metabolite spectrum, a signal represented in the spectrum of metabolite that has large amplitude due to moisture or lipids needs to be removed.

A related art method uses a radio frequency (RF) pulse and a suppression band, to restrict the extraneous signal. However, it is difficult to set a suitable suppression band to accurately remove the signals influenced by fat. Also, it is a problem that a signal of a metabolite of interest may be reduced by the application of the suppression band.

Another related art method generates an additional magnetic resonance image to obtain an additional fat image and remove the fat related signal. However, generation of an additional MR image is cumbersome and expensive.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide a method of removing distortion by lipid from an MR image.

According to an aspect of an exemplary embodiment, there is provided a method of removing distortion by lipids from an MR image which includes obtaining an MR image including at least one voxel, obtaining data of each voxel from the obtained MR image, estimating a lipid-related spectrum by using the obtained data, and removing the estimated lipid-related spectrum from the obtained data.

The obtaining of the data of each voxel from the obtained MR image may include obtaining spectrum data of each voxel and generating at least one of a map indicating an amount of metabolite and a map indicating an amount of lipid included in each voxel by using the obtained spectrum data.

The estimating of the lipid-related spectrum by using the obtained data may include obtaining first lipid data by using the map indicating the amount of the lipid, obtaining metabolite data by using the map indicating the amount of the metabolite, obtaining second lipid data by removing the obtained metabolite data from the obtained first lipid data, and estimating the lipid-related spectrum by using the obtained spectrum data of each voxel from the obtained MR image and the obtained second lipid data.

The obtaining of the first lipid data by using the map indicating the amount of the lipid may include setting a mask including at least one voxel satisfying a predetermined criteria in the map indicating the amount of the lipid, and obtaining a spectrum of the at least one voxel included in the set mask as the first lipid data for the at least one voxel included in the set mask.

The predetermined criteria may include a ratio of lipid included in a voxel to a maximum amount of lipid allowed in the voxel.

The obtaining of the first lipid data for the at least one voxel by using the map indicating the amount of the lipid further may include reconfiguring the first lipid data for the at least one voxel included in the set mask by a singular value decomposition (SVD) process.

The obtaining of the metabolite data by using the map indicating the amount of the metabolite may include setting a mask including at least one voxel having an amount of metabolite larger than that of lipid, and obtaining a spectrum of the at least one voxel having the amount of metabolite larger than that of lipid as metabolite data.

The obtaining of the metabolite data by using the map indicating the amount of the metabolite may further include reconfiguring the metabolite data by the SVD process.

The obtaining of the metabolite data by using the map indicating the amount of the metabolite may further include extracting a spectrum having a maximum peak value among spectrums of the reconfigured metabolite data, and determining the extracted spectrum as the metabolite data.

The obtaining of the second lipid data for the at least one voxel by removing the obtained metabolite data from the obtained first lipid data may include determining correlation of the reconfigured metabolite data and the reconfigured first lipid data, selecting the reconfigured first lipid data for the at least one voxel included in the set mask based on a predetermined value and the determined correlation, and obtaining the second lipid data by removing the obtained metabolite data from the selected reconfigured first lipid data for the at least one voxel included in the set mask.

The predetermined value may be determined based on at least one of a ratio of lipid included in the obtained metabolite data and a loss rate of the obtained metabolite data which includes the obtained spectrum data of each voxel of the MR image.

The estimating of the lipid-related spectrum by using the spectrum data of each voxel of the MR image and the obtained second lipid data may include estimating the lipid-related spectrum by projecting the spectrum data of each voxel of the MR image to the obtained second lipid data.

The removing of the estimated lipid-related spectrum from the obtained data may include removing the estimated lipid-related spectrum from the obtained spectrum data of each voxel of the MR image.

According to another aspect of an exemplary embodiment, there is provided an apparatus for removing distortion by lipids from an MR image which includes an image obtainer configured to obtain an MR image including at least one voxel, a voxel data obtainer configured to obtain data of each voxel from the obtained MR image, a spectrum estimator configured to estimate a lipid-related spectrum by using the obtained data, and an editor configured to remove the estimated lipid-related spectrum from the obtained data.

The voxel data obtainer may include a spectrum obtainer configured to obtain spectrum data of each voxel, and a map generator configured to generate at least one of a map indicating an amount of metabolite and a map indicating an amount of lipid included in each voxel by using the obtained spectrum data.

The spectrum estimator may include a first lipid data obtainer configured to obtain first lipid data by using the map indicating the amount of the lipid, a metabolite data obtainer configured to obtain metabolite data by using the map indicating the amount of the metabolite, and a second lipid data obtainer configured to obtain second lipid data by removing the obtained metabolite data from the obtained first lipid data.

The spectrum estimator may estimate the lipid-related spectrum by using the obtained spectrum data of each voxel from the obtained MR image and the obtained second lipid data.

The first lipid data obtainer may include a lipid mask determiner configured to set a mask including at least one voxel satisfying a predetermined criteria in the map indicating the amount of the lipid.

The first lipid data obtainer may obtain a spectrum of the at least one voxel included in the set mask as the first lipid data for the at least one voxel included in the set mask.

The predetermined criteria may include a ratio of lipid included in a voxel to a maximum amount of lipid allowed in the voxel.

The first lipid data obtainer may further include a lipid data reconfigurator configured to reconfigure the first lipid data for the at least one voxel included in the set mask by an SVD process.

The metabolite data obtainer may include a metabolite data mask determiner configured to set a mask including at least one voxel having an amount of metabolite larger than that of lipid.

The metabolite data obtainer may obtain a spectrum of the at least one voxel having the amount of metabolite larger than that of lipid as metabolite data.

The metabolite data obtainer may further include a metabolite data reconfigurator configured to reconfigure the metabolite data by the SVD process.

The metabolite data obtainer may further include an extractor configured to extract a spectrum having a maximum peak value among spectrums of the reconfigured metabolite data, and a determiner configured to determine the extracted spectrum as the metabolite data.

The second lipid data obtainer may include a correlation determiner configured to determine correlation of the reconfigured metabolite data and the reconfigured first lipid data, and a selector configured to select the reconfigured first lipid data for the at least one voxel included in the set mask based on a predetermined value and the determined correlation.

The second lipid data obtainer may obtain the second lipid data by removing the obtained metabolite data from the selected reconfigured first lipid data for the at least one voxel included in the set mask.

The apparatus may further include a value determiner configured to determine the predetermined value based on an external input.

The predetermined value may be determined based on at least one of a ratio of lipid included in the obtained metabolite data and a loss rate of the obtained metabolite data which includes the obtained spectrum data of each voxel of the MR image.

The spectrum estimator may estimate the lipid-related spectrum by projecting the spectrum data of each voxel of the MR image to the obtained second lipid data.

The editor may remove the estimated lipid-related spectrum from the obtained spectrum data of each voxel of the MR image.

According to another aspect of an exemplary embodiment, there is provided a non-transitory computer readable storage medium having stored thereon a program, when executed by a computer, performs the method of removing distortion by lipids from an MR image which includes obtaining an MR image including at least one voxel, obtaining data of each voxel from the obtained MR image, estimating a lipid-related spectrum by using the obtained data, and removing the estimated lipid-related spectrum from the obtained data.

BRIEF DESCRIPTION OF THE DRAWINGS

The above and/or other aspects will become more apparent by describing certain exemplary embodiments with reference to the accompanying drawings, in which:

FIGS. 7A and 7B illustrate examples of the obtained first lipid data and the reconfigured first lipid data, according to an exemplary embodiment;

DETAILED DESCRIPTION

Figure 1:
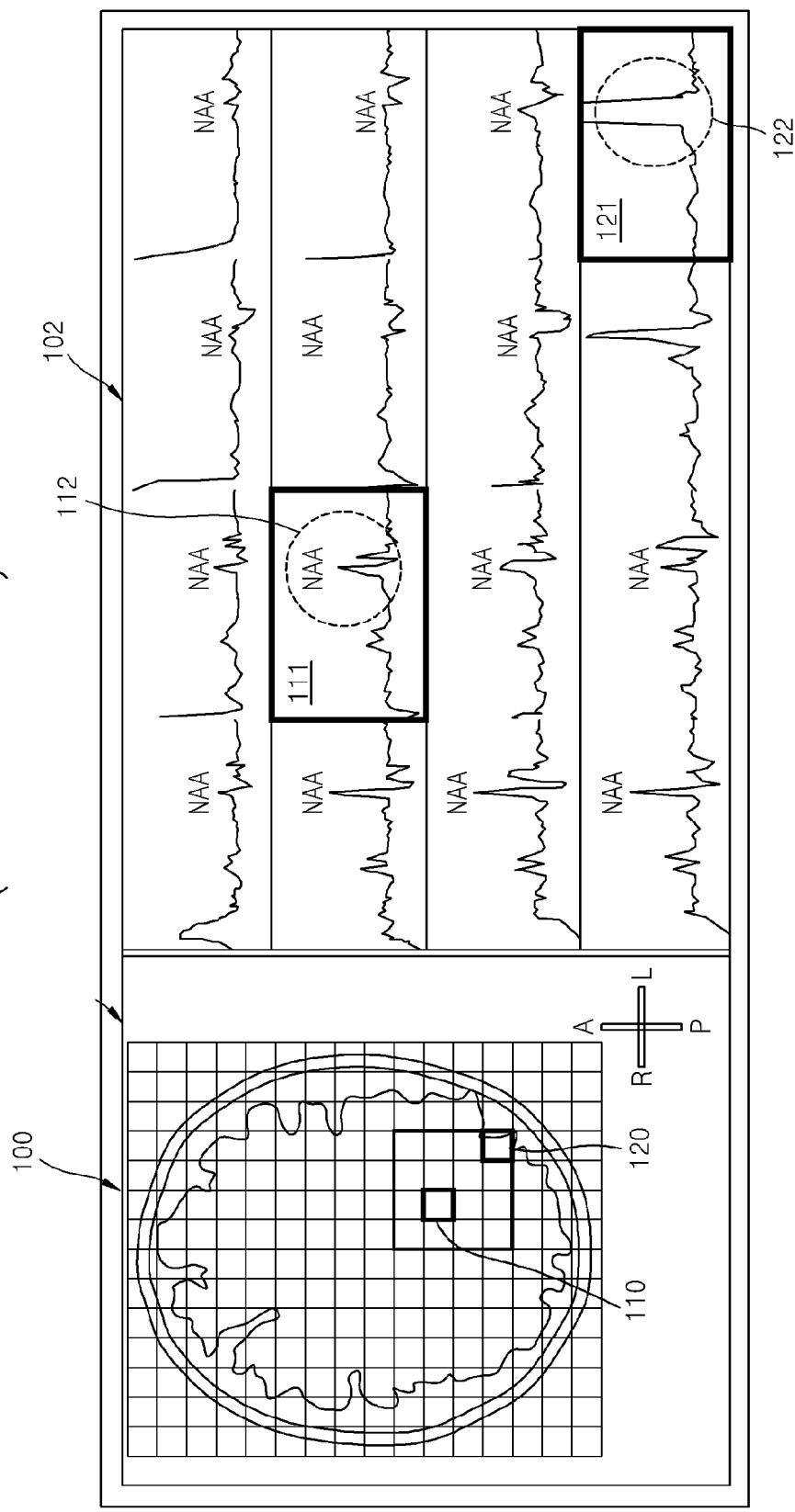
FIG. 1 illustrates an MR image obtained by using a related art MR image capturing apparatus and a spectrum of voxels included in the MR image.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

The terms used in the present specification are used for explaining exemplary embodiments, and are not limiting. Thus, the expression of singularity includes the expression of plurality unless clearly specified otherwise in context. Unless defined otherwise, all terms used herein including technical or scientific terms have the same meanings as those generally understood by those skilled in the art. The terms as those defined in generally used dictionaries are construed to have meanings matching that in the context of related technology and, unless clearly defined otherwise, are not construed to be ideally or excessively formal.

When a part may "include" a certain constituent element, unless specified otherwise, it may not be construed to exclude another constituent element but may be construed to further include other constituent elements. The terms such as "portion", "unit", "module", and "block" stated in the specification may signify a unit to process at least one function or operation and the unit may be embodied by hardware, software, or a combination of hardware and software.

As used herein, the term "and/or" includes any and all combinations of one or more of the associated listed items. Expressions such as "at least one of," when preceding a list of elements, modify the entire list of elements and do not modify the individual elements of the list.

In MRSI of a brain, it is difficult to accurately measure an amount of metabolite of the brain due to a lipid signal having large amplitude. The lipid signal may be generated not from a brain tissue but from subcutaneous tissue, scalp, and bone marrow, which are all located outside the brain.

Among different methods, a method of exciting and removing a fat signal in an area where a target to be removed is located, by using a radio frequency (RF) pulse, is the most frequently used for fat suppression. However, the method has difficulty setting a suppression band suitable for anatomy and thus it is difficult to efficiently remove the influence of fat. Also, it is a problem that a signal of a metabolite of interest may be reduced by the influence of a suppression band.

To reduce the influence of fat, the shape of a fat signal may be estimated and removed by using an additional MR image or information and thus the influence of the fat signal may be omitted from an overall MR image. For example, the influence by a fat signal may be removed by obtaining an additional fat weighted image or by forming the shape of a fat signal in a space domain by using actually obtained MRSI data.

Also, there is a method of reducing the influence of a fat signal to be removed from an MR spectrum at a desired position of an MR image, for example, a position of a voxel. This is accomplished by generating a brain mask and a fat mask through an additional MR image and filling high spatial k-space data that is obtained without using extrapolation method in the MRSI data so that a fat signal may restrict only the fat mask in the MRSI data.

A spatial sidelobe may be large compared to magnetic resonance imaging (MRI) due to the influence of a large size of a voxel used for MRSI. For example, in brain MRSI, a spatial sidelobe generated by lipids located in subcutaneous tissue, scalp, and bone marrow, which are all located outside a brain, may influence a spectrum generated in the brain. The influence of a spatial sidelobe by lipids may be insignificant in an area deep in the brain in comparison to an area close to a lipid source such as cortex.

For example, in case of N-acetylaspartate (NAA), it is important to reduce a spatial sidelobe of lipids in regularizing the amount of NAA because a position of NAA, such as 2.0 ppm, in a spectrum may be close to a position of a lipid component, such as 0.9-1.3 ppm, in the spectrum. However, in the above-described methods, an additional MR image may be needed, an accurate position of lipids needs to be identified when using an extrapolation method, and a metabolite signal may be removed when a lipid signal is removed from a MR image by using the distribution pattern of lipids in the MR image.

FIG. 1 schematically illustrates an MR image 100 obtained by using a related art MR image capturing apparatus and a spectrum 102 of voxels included in the MR image. Spectrum data of a voxel of interest (VOI) may be obtained from the MR image 100 of a brain. For example, as illustrated in FIG. 1, spectrum data of VOIs having a size of 4×4 may be obtained from an MR image of a brain.

For example, it may be difficult to identify a metabolite signal in a voxel 120 included in an area of a skull because a lipid signal of a considerable amount generated by lipids in subcutaneous tissue is mixed with the metabolite signal. For example, there may be an area 122 in which NAA is mixed with a lipid signal and thus is not identified in spectrum data 121 regarding the voxel 120.

Also, the distinction between the metabolite signal and the lipid signal may be difficult as the lipid signal spreads toward a voxel 110 that is included in a central area of a brain separated far from the skull, due to Gibb's ringing. For example, NAA and the lipid signal appear close to each other in spectrum data 111 of the voxel 110 and thus there may be an area 112 in which accurate measurement of NAA is difficult because the lipid signal is mixed with the NAA signal.

Figure 2:
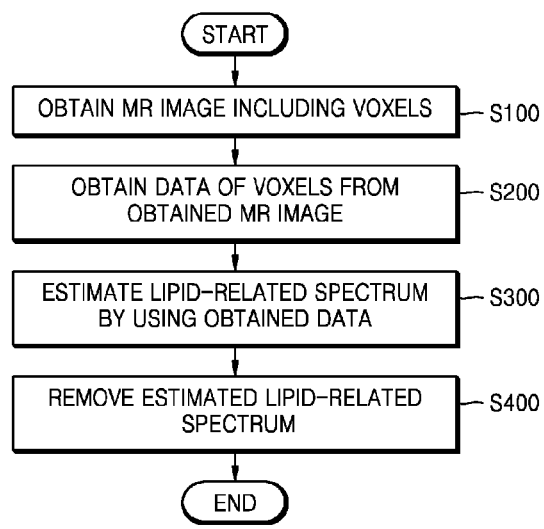
FIG. 2 is a flowchart for explaining a method of removing distortion by lipids from an MR image, according to an exemplary embodiment.

FIG. 2 is a flowchart for explaining a method of removing distortion by lipids from an MR image, according to an exemplary embodiment. Referring to FIG. 2, the method of removing distortion by lipids from an MR image according to the present exemplary embodiment may include obtaining an MR image including at least one voxel (operation S100), obtaining data of each voxel from the obtained MR image (operation S200), estimating a lipid-related spectrum by using the obtained data (operation S300), and removing an estimated lipid-related spectrum from the obtained data (operation S400).

An MR image according to the present exemplary embodiment may include an MR spectroscopic image.

Figure 3:
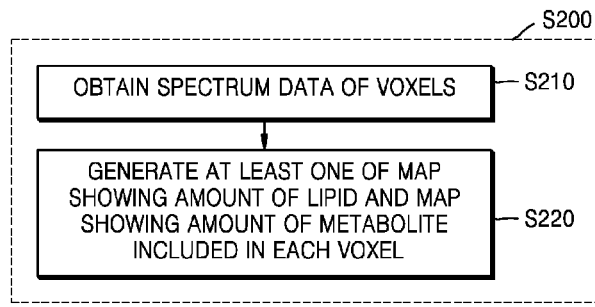
FIG. 3 is a flowchart for explaining an example of the operation S200 of FIG. 2 of obtaining data of each voxel from the obtained MR image, according to an exemplary embodiment.

FIG. 3 is a flowchart for explaining an example of the operation S200 of FIG. 2 of obtaining data of each voxel from the obtained MR image, according to an exemplary embodiment. Referring to FIG. 3, the operation S200 may include obtaining spectrum data of each voxel (operation S210) and generating at least one of a map showing an amount of lipid and a map showing an amount of metabolite included in each voxel by using the obtained spectrum data (operation S220).

Figure 4B:
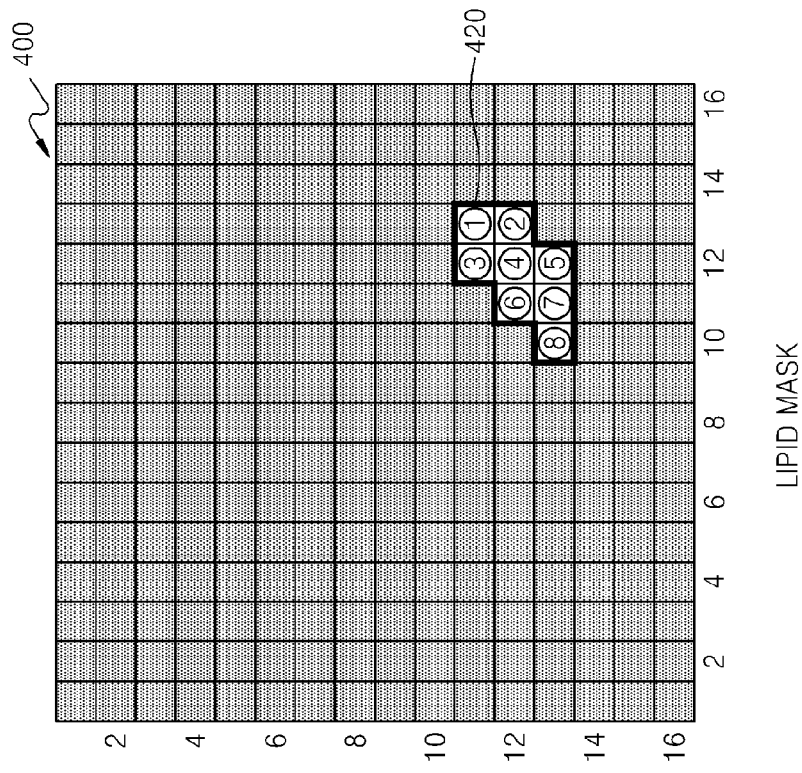
FIGS. 4A and 4B respectively illustrate a lipid map and a lipid mask, according to an exemplary embodiment.
Figure 4A:
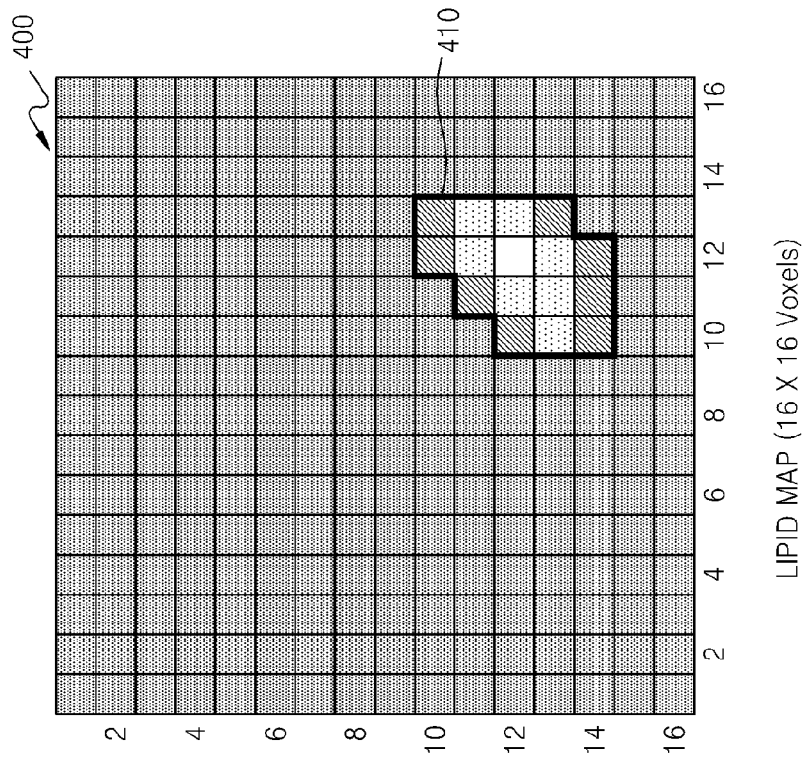

FIGS. 4A and 4B respectively illustrate a lipid map and a lipid mask, according to an exemplary embodiment. For example, when the spectrum data of each voxel in an MR image is obtained, an amplitude of lipid signal is obtained from each spectrum data and an amount of lipid included in each voxel may be shown based on the obtained amplitude of lipid signal. The amount of lipid may be represented as a change in brightness of a voxel. For example, a portion having the maximum amount of lipid may appear to be the brightest, whereas a portion having the minimum amount of lipid may appear to be the darkest.

Data indicating the distribution of lipid may be defined as a lipid map. For example, a lipid map 400 including a 16×16 grid of voxels and showing a distribution of lipid as a difference in brightness may be generated as illustrated in FIG. 4A.

The lipid mask 420 as illustrated in FIG. 4B may be defined from the lipid map 400 by using a predetermined area of voxels 410, the voxels in the predetermined area of voxels each including a predetermined amount of lipid, which will be described below with reference to FIGS. 5 and 6.

Figure 5:
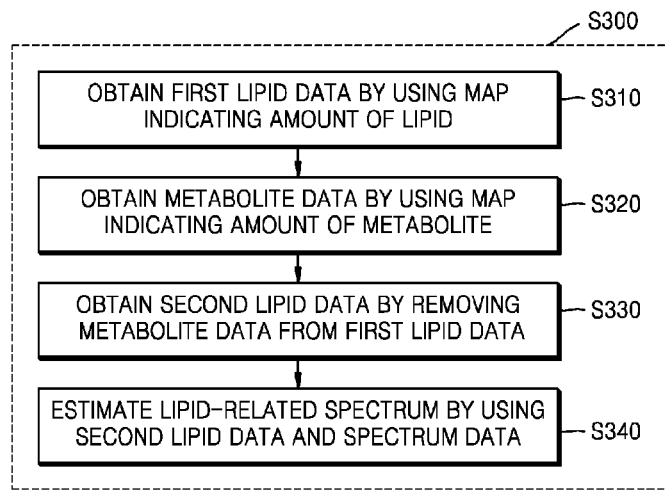
FIG. 5 is a flowchart for explaining an example of estimating a lipid-related spectrum by using the obtained data, according to an exemplary embodiment.

FIG. 5 is a flowchart for explaining an example of the operation S300 of FIG. 2 of estimating a lipid-related spectrum by using the obtained data, according to an exemplary embodiment. Referring to FIG. 5, the operation S300 of estimating a lipid-related spectrum by using the obtained data according to the present exemplary embodiment may include obtaining first lipid data by using a map indicating an amount of lipid (operation S310), obtaining metabolite data by using a map indicating an amount of metabolite (operation S320), obtaining second lipid data by removing the obtained metabolite data from obtained first lipid data (operation S330), and estimating a lipid-related spectrum by using obtained second lipid data and spectrum data of each voxel of an MR image (operation S340).

Figure 6:
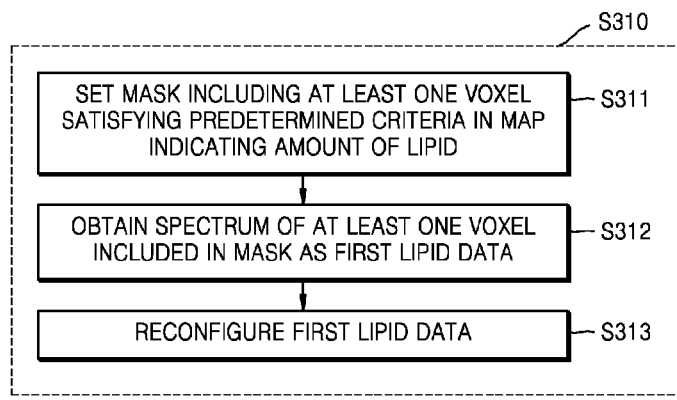
FIG. 6 is a flowchart for explaining an example of obtaining first lipid data by using a map indicating the amount of lipid, according to an exemplary embodiment.

FIG. 6 is a flowchart for explaining an example of the operation S310 of FIG. 5 of obtaining the first lipid data by using a map indicating the amount of lipid, according to an exemplary embodiment. Referring to FIG. 6, the operation S310 may include setting a mask including at least one voxel satisfying a predetermined criteria based on the map indicating the amount of generated lipids (operation S311) and obtaining a spectrum of the at least one voxel included in the mask as the first lipid data (operation S312).

The predetermined criteria according to the present exemplary embodiment may include a rate of the maximum amount of lipid that may be included in a voxel. The operation S310 may further include reconfiguring the first lipid data through an SVD process (operation S313).

FIG. 7 illustrates examples of the obtained first lipid data and the reconfigured first lipid data obtained through an SVD process, according to an exemplary embodiment. FIG. 7A shows lipid spectrum data of voxels included in the lipid mask and FIG. 7B shows a reconfiguration result of the lipid spectrum data of voxels included in the lipid mask through the SVD process.

For example, the lipid spectrum data M in the SVD process may be expressed by Equation 1.

$$M = U \Sigma V^*$$ [Equation 1]

For example, in Equation 1, U denotes a left singular vector, $\Sigma$ denotes a singular value, V denotes a right singular vector, and * (asterisk) denotes the complex conjugate of a complex number. The lipid spectrum data M may be expressed by a multiplication of U, $\Sigma$, and V, and diagonal components of $\Sigma$ may be expressed as a singular value base vector of the lipid spectrum data.

As described above with reference to FIG. 4, when spectrum data of each voxel of an MR image is obtained, the lipid map 400 may be generated by using the obtained spectrum data.

The predetermined area of voxels 410 may be determined according to a ratio with respect to the maximum amount of lipid that may be included per voxel in the generated lipid map. For example, voxels including lipids in an amount larger than 30% of the maximum amount of lipid allowed per voxel may be selected as a group. Furthermore, as an amount of lipid included in a voxel becomes larger, the voxel may appear to be brighter in the lipid map 400.

The group of selected voxels includes a considerable amount of lipid and may be defined as a lipid mask 420 to obtain the first lipid data.

For example, as illustrated in FIG. 4B, eight voxels may be included in the lipid mask 420. For convenience of explanation, each voxel is numbered 1, 2, 3, 4, 5, 6, 7, and 8.

In other words, as illustrated in FIG. 6, the operation S310 of obtaining the first lipid data by using the lipid map 400 that indicates the amount of lipid according to the present exemplary embodiment may include setting a mask including at least one voxel satisfying a predetermined criteria in a map indicating the amount of generated lipid (operation S311) and obtaining a spectrum of at least one voxel included in the mask as the first lipid data (operation S312).

Spectrum data of each voxel 1, 2, 3, 4, 5, 6, 7, and 8 included in the lipid mask 420 may be obtained. Referring to FIG. 7A, spectrum of voxels 1, 2, 3, and 4 included in the lipid mask 420 is illustrated, as an example. Referring to FIGS. 4A and 4B, a voxel 4 in the lipid mask of FIG. 4B is the brightest voxel. Thus, the amplitude of a lipid spectrum of the voxel 4 may be the greatest, as illustrated in FIG. 7A.

The operation S310 may further include reconfiguring the obtained first lipid data through the SVD process, for example, for voxels 1, 2, 3, 4 5, 6, 7, and 8. As illustrated in FIG. 7B, a spectrum of voxels 1, 2, 3, and 4 included in the lipid mask 420 of FIG. 4B may be reconfigured or normalized as first lipid data sets 230, 232, 234, and 236 in correspondence with the spectrum data of voxels 1, 2, 3, and 4, shown in FIG. 7B as an example. For example, the spectrum of voxels included in the lipid mask 420 of FIG. 4B may be reconfigured through the SVD process or another appropriate process.

Figure 8:
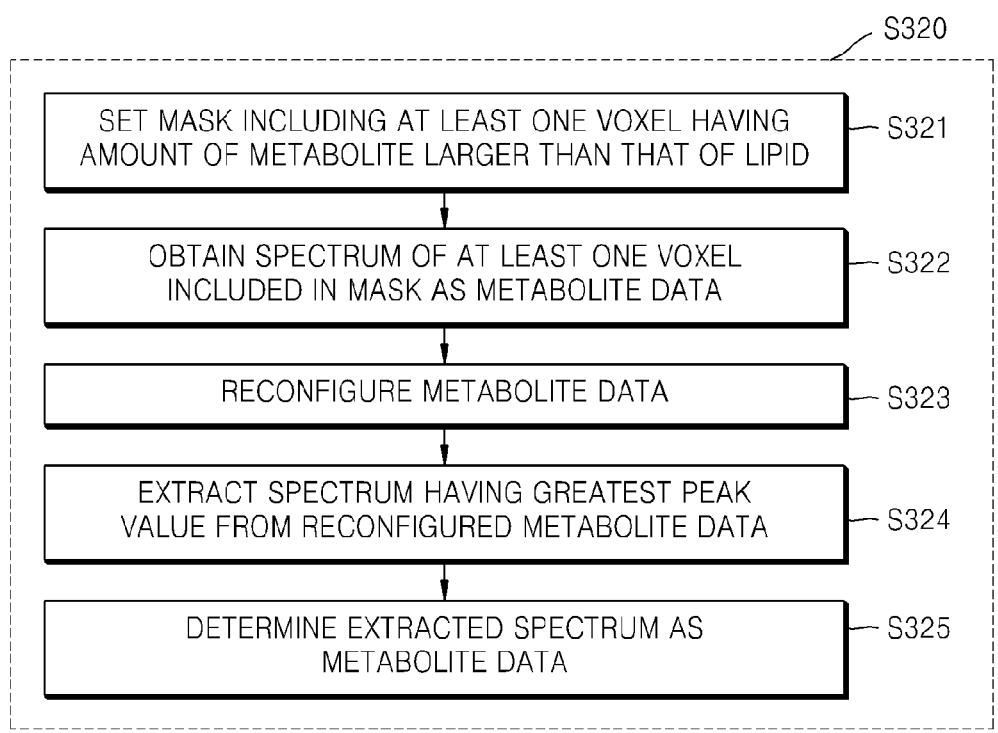
FIG. 8 is a flowchart for explaining an example of obtaining metabolite data by using a map indicating the amount of metabolite, according to an exemplary embodiment.

FIG. 8 is a flowchart for explaining an example of the operation of S320 of FIG. 5 of obtaining metabolite data by using a map 900 of FIG. 9 indicating the amount of metabolite, according to an exemplary embodiment. The operation S320 may include setting a metabolite mask 920 including at least one voxel having an amount of metabolite larger than that of lipids (operation S321) and obtaining a spectrum of the at least one voxel included in the metabolite mask 920 as metabolite data (operation S322).

The operation S320 may further include reconfiguring the metabolite data through the SVD process (operation S323), extracting a spectrum having the greatest peak value from the reconfigured metabolite data (operation S324), and determining an extracted spectrum as metabolite data (operation S325).

FIGS. 9A, 9B, 9C, and 9D illustrate the metabolite data obtained according to an exemplary embodiment and an example of metabolite data reconfigured through an SVD process.

The operation S320 of FIG. 8 of obtaining metabolite data by using the metabolite map 900 indicating the amount of metabolite according to the present exemplary embodiment is similar to the operation S310 of FIG. 6 of obtaining the first lipid data by using the lipid map 400 of FIG. 4A.

Figure 9A:
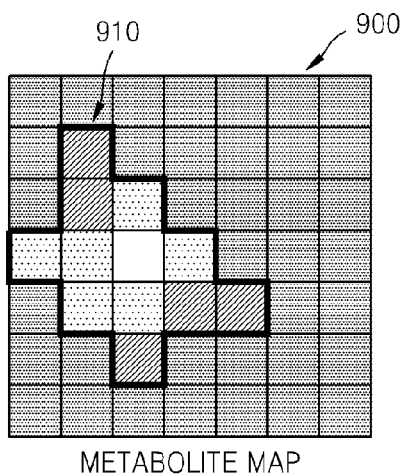
FIGS. 9A, 9B, 9C, and 9D illustrate the metabolite data obtained according to an exemplary embodiment and an example of metabolite data reconfigured through an SVD process.

FIG. 9A illustrates the metabolite map 900 in an array of 16×16 voxels, by presenting a distribution of metabolite by using a difference in brightness. The brightness may vary according to the distribution of metabolite. A predetermined area 910 on the metabolite map 900 may be determined by a similar method as one used for the determination of the predetermined area 410 of the lipid map 400. The metabolite mask 920 may be defined from the predetermined area 910.

Figure 9B:
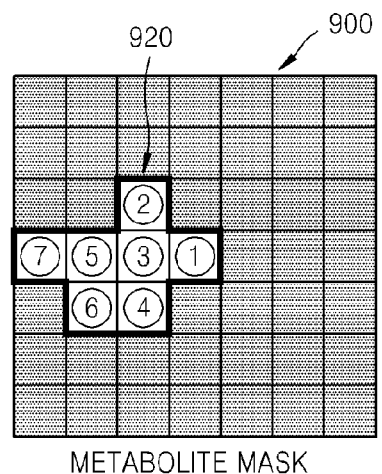

For example, as illustrated in FIG. 9B, the metabolite mask 920 defined according to a predetermined amount of metabolite may include seven voxels.

Figure 9C:
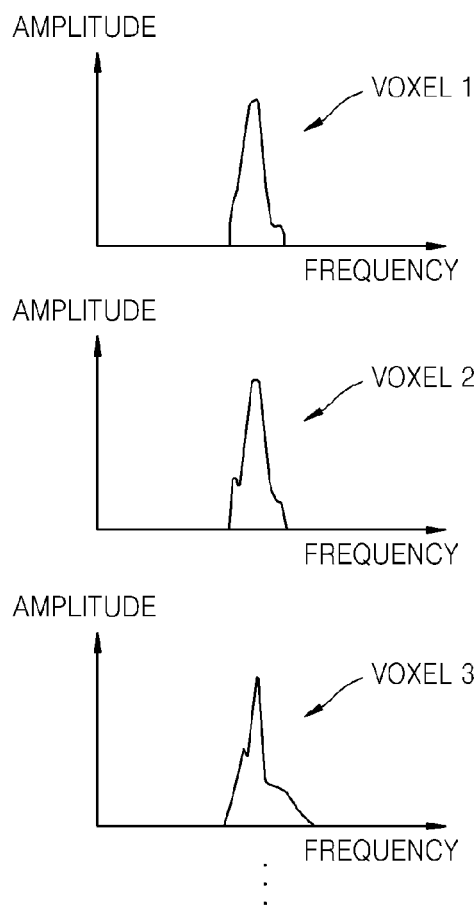
Figure 9D:
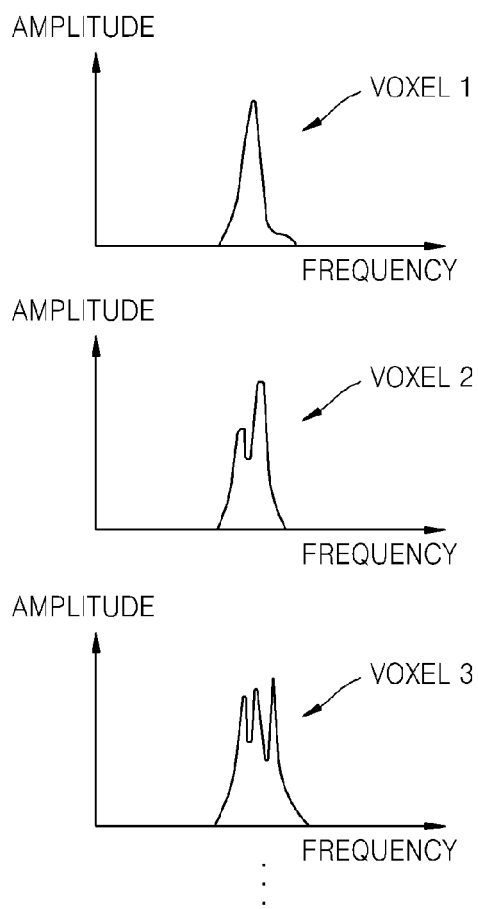

Spectrum data may be obtained for each of the seven voxels included in the metabolite mask 920. FIG. 9C illustrates spectrum data for the voxels 1, 2, and 3 included in the metabolite mask 920, as an example. The spectrum data obtained for each of the seven voxels included in the metabolite mask 920 may be reconfigured through the SVD process or another appropriate process. FIG. 9D illustrates the reconfigured data spectrum data for the voxels 1, 2, and 3, as an example.

According to the present exemplary embodiment, a spectrum having the maximum peak value may be extracted from among the reconfigured spectrum data for each of the seven voxels in the metabolite data reconfigured in the operation S324. However, an exemplary embodiment is not limited thereto. For example, the top five spectrums including the maximum peak value and thus an extracted spectrum (or spectra) from among the reconfigured spectrum data may be determined as metabolite data. That is, the spectrum having the maximum peak value or the top five spectrums including the maximum peak value may be selected as metabolite data.

Figure 10:
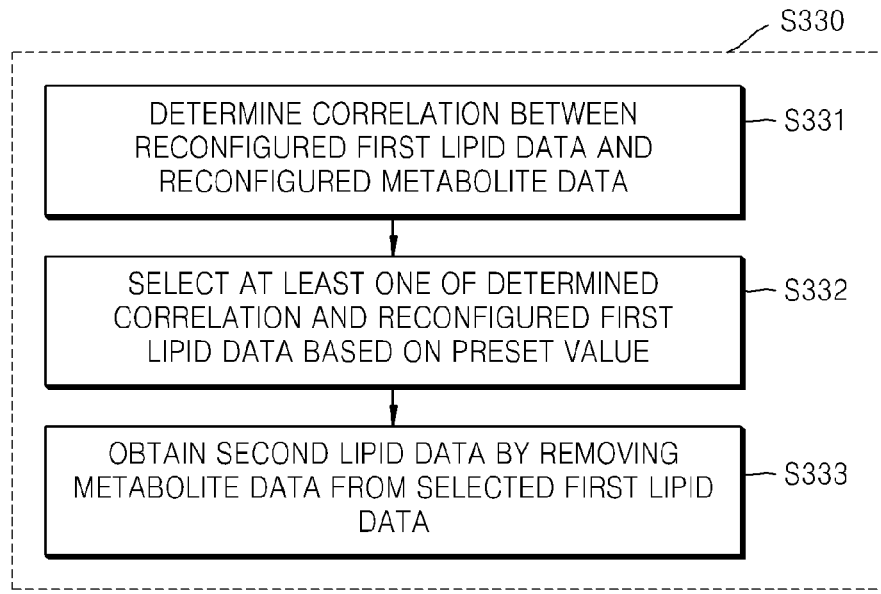
FIG. 10 is a flowchart for explaining the obtaining second lipid data by removing the reconfigured metabolite data from the reconfigured first lipid data, according to an exemplary embodiment.

FIG. 10 is a flowchart for explaining the operation S330 of FIG. 5 of obtaining second lipid data by removing the reconfigured metabolite data from the reconfigured first lipid data, according to an exemplary embodiment.

The operation S330 of obtaining the second lipid data by removing the metabolite data obtained from the obtained first lipid data according to the present exemplary embodiment may include determining a correlation between the reconfigured first lipid data and the reconfigured metabolite data (operation S331), selecting at least one of a determined correlation and the first lipid data reconfigured based on a preset value (operation S332), and obtaining the second lipid data by removing the metabolite data obtained from a selected first lipid data (operation S333).

A preset value according to the present exemplary embodiment may be determined based on at least one of a loss rate of the metabolite data and a ratio of lipids to the metabolite data in the spectrum data of each voxel of an MR image.

Figure 11:
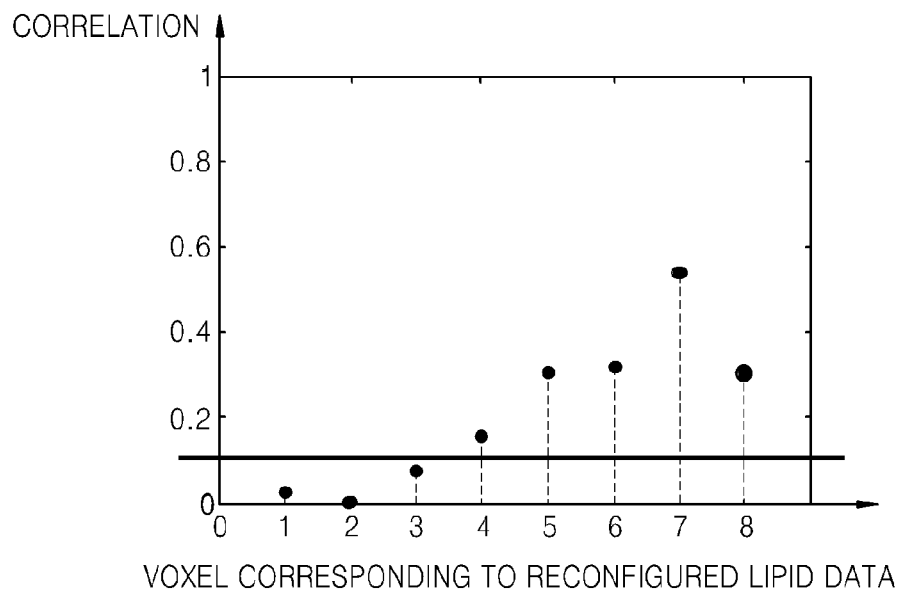
FIG. 11 is a graph showing an example of a preset value and a correlation between the reconfigured metabolite data and the reconfigured first lipid data, according to an exemplary embodiment.

FIG. 11 is a graph showing an example of a preset value and a correlation between the reconfigured metabolite data and the reconfigured first lipid data, according to an exemplary embodiment. In FIG. 11, a vertical axis denotes a correlation value and a horizontal axis denotes a voxel corresponding to the reconfigured first lipid data.

The voxel on the horizontal axis, for example, a voxel corresponding to the reconfigured first lipid data set 230 of FIG. 7B, may be indexed to voxel 1, in FIG. 11. In a similar manner, the reconfigured first lipid data sets 232, 234, 236 of FIG. 7B may be respectively indexed to voxels 2, 3, and 4, in FIG. 11. The reconfigured first lipid data sets corresponding to voxels 5, 6, 7, and 8, although not shown in FIG. 7B, may be respectively indexed to voxels 5, 6, 7, and 8 in FIG. 11.

A correlation value is an index of correlation, and a high correlation value signifies that data has high relevancy. Thus, when a correlation value is high, it signifies that most of the metabolite data may be included in the first lipid data and likewise most of the first lipid data may be included in the metabolite data.

Thus, the first lipid data corresponding to a voxel having a high correlation value is not used to estimate a lipid-related spectrum. To this end, a preset value to determine whether a correlation value is high may be needed.

In other words, the preset value may refer to a correlation determination reference value to obtain the second lipid data from the first lipid data while minimally affecting the metabolite data.

According to the present exemplary embodiment, the first lipid data of a voxel in which the correlation value is not greater than the preset value may be used to estimate the lipid-related spectrum. For example, the first lipid data reconfigured with respect to voxels 1, 2, and 3 in FIG. 11 may be selected to obtain the second lipid data.

Figure 12A:
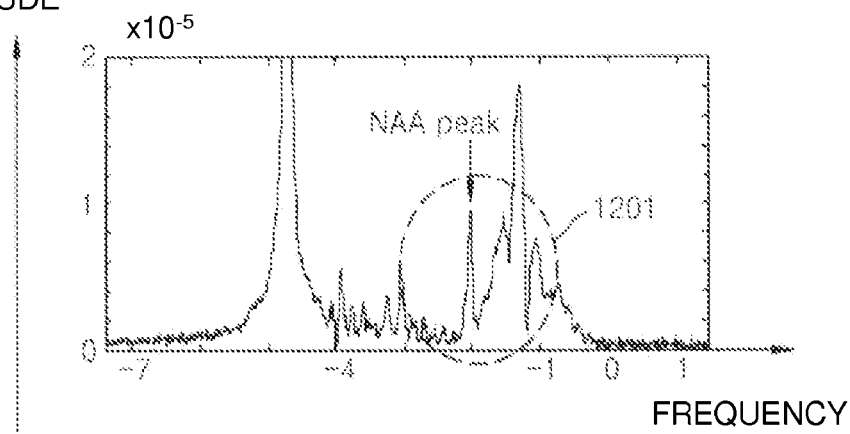
FIGS. 12A, 12B, and 12C illustrate removing a lipid-related spectrum that is estimated according to a preset value.

FIG. 12 illustrates a degree of removing a lipid-related spectrum that is estimated according to a preset value. Referring to FIG. 12A, when the preset value is too low, the reconfigured first lipid data may not be selected at all and thus a lipid spectrum component located around an NAA peak may not be removed (area 1201).

Figure 12B:
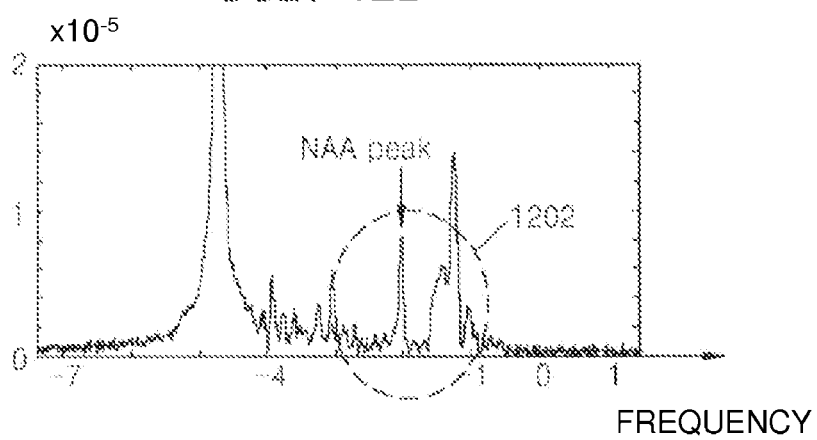
Figure 12C:
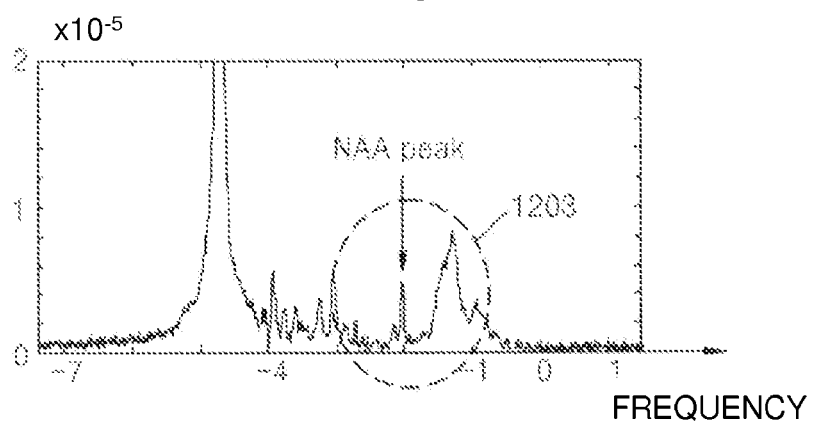

Referring to FIG. 12C, when the preset value is too high, most of the reconfigured first lipid data is selected and thus a large amount of a lipid spectrum component may be removed. However, a spectrum of a voxel having a high correlation value may be selected and thus the metabolite data may be removed together with the lipid component (area 1203).

Thus, as illustrated in a circled area 1202 of FIG. 12B, when the preset value is appropriate, the lipid spectrum component is substantially or entirely removed and reliability of the metabolite spectrum is improved.

Referring back to FIG. 5, the operation S340 of estimating a lipid-related spectrum by using the obtained second lipid data and the spectrum data of each voxel of an MR image may include estimating a lipid-related spectrum by projecting spectrum data of each voxel of an MR image to the obtained second lipid data.

For example, estimating the lipid-related spectrum may refer to a process of estimating a lipid-related spectrum based on an area that is overlapped due to projecting the obtained second lipid data onto the spectrum data of each voxel of an MR image.

Referring back to FIG. 2, the operation S400 of removing an estimated lipid-related spectrum from the obtained data may include removing the estimated lipid-related spectrum from the obtained spectrum data with respect to each voxel of the MR image.

Figure 13:
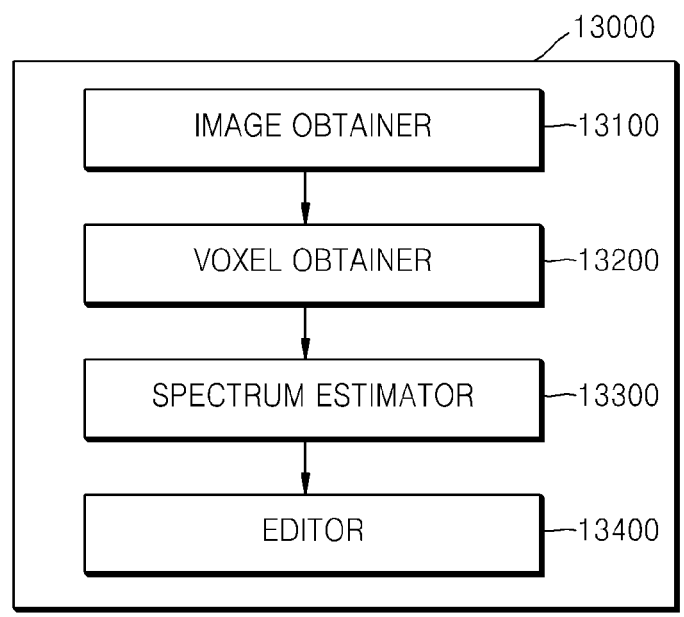
FIG. 13 is a block diagram of an apparatus for removing distortion by lipids from an MR image, according to an exemplary embodiment.

FIG. 13 is a block diagram of an apparatus 13000 for removing distortion by lipids from an MR image, according to an exemplary embodiment. Referring to FIG. 13, the apparatus 13000 for removing distortion by lipids from an MR image according to the present exemplary embodiment may include an image obtainer 13100 obtaining an MR image including at least one voxel, a voxel data obtainer 13200 obtaining data of each voxel from an obtained MR image, a spectrum estimator 13300 estimating a lipid-related spectrum by using obtained data, and an editor 13400 removing a lipid-related spectrum estimated from the obtained data.

In the present exemplary embodiment, the MR image obtained by the image obtainer 13100 may include an MR spectroscopic image.

Figure 14:
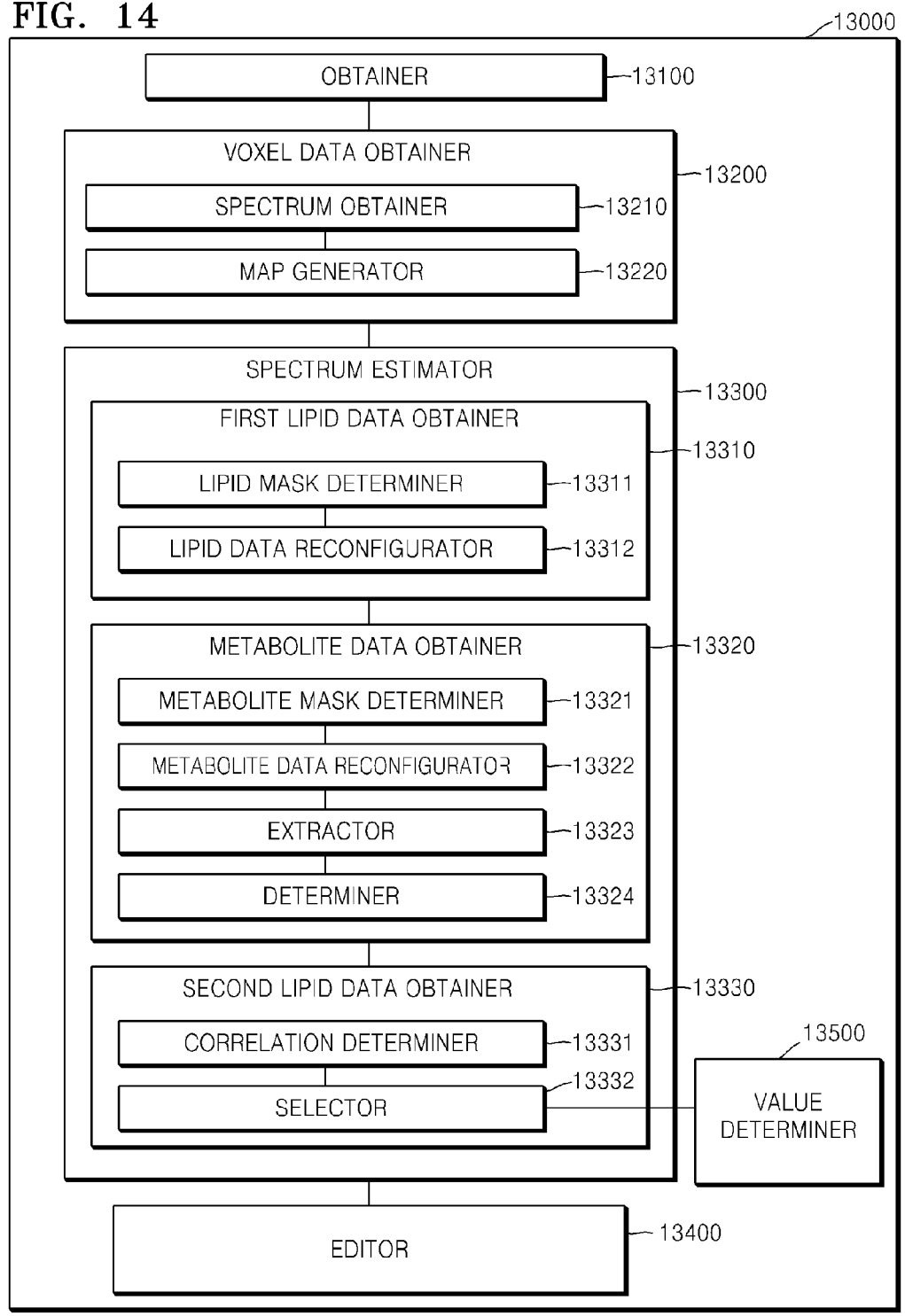
FIG. 14 is a more detailed block diagram of an apparatus for removing distortion by lipids from an MR image, according to an exemplary embodiment.

FIG. 14 is a block diagram of an apparatus for removing distortion by lipids from an MR image, according to another exemplary embodiment. Referring to FIG. 14, the voxel data obtainer 13200 according to the present exemplary embodiment includes a spectrum obtainer 13210 obtaining spectrum data of each voxel and a map generator 13220 generating at least one of a map indicating the amount of metabolite and a map indicating the amount of lipid included in each voxel by using the obtained spectrum data.

The spectrum estimator 13300 according to the present exemplary embodiment may include a first lipid data obtainer 13310 obtaining first lipid data by using a map indicating the amount of lipid, a metabolite data obtainer 13320 obtaining metabolite data by using a map indicating metabolite data and by using a map indicating the amount of metabolite, and a second lipid data obtainer 13330 obtaining second lipid data by removing the metabolite data obtained from the obtained first lipid data.

The spectrum estimator 13300 may estimate a lipid-related spectrum by using the spectrum data of each voxel of an MR image and the obtained second lipid data.

The first lipid data obtainer 13310 according to the present exemplary embodiment may include a lipid mask determiner 13311 setting a mask including at least one voxel satisfying a predetermined criteria in a map indicating the amount of lipid.

The first lipid data obtainer 13310 may obtain a spectrum of at least one voxel included in the mask as the first lipid data.

The predetermined criteria according to the present exemplary embodiment may include a ratio of lipid included in a voxel to the maximum amount of lipid allowed in the voxel.

The first lipid data obtainer 13310 may further include a lipid data reconfigurator 13312 that reconfigures the first lipid data by a SVD process.

The metabolite data obtainer 13320 according to the present exemplary embodiment may include a metabolite mask determiner 13321 that sets a mask including at least one mask having an amount of metabolite larger than that of lipid.

The metabolite data obtainer 13320 may obtain a spectrum of at least one voxel included in the mask as the metabolite data.

The metabolite data obtainer 13320 may further include a metabolite data reconfigurator 13322 that reconfigures the metabolite data by the SVD process.

The metabolite data obtainer 13320 may further include an extractor 13323 extracting a spectrum having the maximum peak value of the reconfigured metabolite data and a determiner 13324 determining an extracted spectrum as metabolite data.

The second lipid data obtainer 13330 according to the present exemplary embodiment may include a correlation determiner 13331 determining correlation between the reconfigured first lipid data and the reconfigured metabolite data and a selector 13332 selecting at least one of a correlation determined by the correlation determiner 13331 and the reconfigured first lipid data based on a preset value.

The second lipid data obtainer 13330 may obtain the second lipid data by removing the obtained metabolite data from the selected first lipid data.

The apparatus 13000 according to the present exemplary embodiment may further include a value determiner 13500 determining a preset value based on an external input.

The preset value according to the present exemplary embodiment may be determined based on at least one of a loss rate of metabolite data and a ratio of lipids to the metabolite data in the spectrum data of each voxel of an MR image.

The spectrum estimator 13300 according to the present exemplary embodiment may estimate a lipid-related spectrum by projecting the spectrum data of each voxel of an MR image to the obtained second lipid data.

The editor 13400 according to the present exemplary embodiment may remove the estimated lipid-related spectrum estimated from the spectrum data obtained from each voxel of an MR image.

The descriptions about the above-described method may be applied to the apparatus according to the present exemplary embodiment. Thus, the descriptions about the apparatus that are the same as those about the method may be omitted.

An exemplary embodiment can also be embodied as computer-readable codes on a computer-readable storage medium. The computer-readable storage medium is any data storage device that can store data which can be thereafter read by a computer system. Examples of the computer-readable storage medium include read-only memory (ROM), random-access memory (RAM), CD-ROMs, magnetic tapes, floppy disks, optical data storage devices, etc. The computer-readable storage medium can also be distributed over network coupled computer systems so that the computer readable code is stored and executed in a distributed fashion.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of removing distortion by lipids from a magnetic resonance (MR) image, the method comprising:
   obtaining an MR image including voxels;
   obtaining data of the voxels from the obtained MR image;
   obtaining a first lipid data based on the obtained data of the voxels;
   obtaining a metabolite data based on the obtained data of the voxels;
   obtaining a second lipid data by removing the obtained metabolite data from the first lipid data;

estimating a lipid-related spectrum by using the obtained second lipid data from which the metabolite data has been removed; and removing the estimated lipid-related spectrum from the obtained data.

2. The method of claim 1, wherein the obtaining the data of the voxels comprises:

obtaining spectrum data of the voxels; and generating a map indicating an amount of metabolite and a map indicating an amount of lipid included in the voxels by using the obtained spectrum data.

3. The method of claim 2, wherein the first lipid data is obtained by using the map indicating the amount of the lipid, and the metabolite data is obtained by using the map indicating the amount of the metabolite, and the estimating the lipid-related spectrum comprises:

estimating the lipid-related spectrum by using the obtained spectrum data of the voxels and the obtained second lipid data.

4. The method of claim 3, wherein the obtaining the first lipid data comprises:

setting a first mask including a voxel satisfying a certain criteria in the map indicating the amount of the lipid; and obtaining a spectrum of the voxel included in the first mask as the first lipid data for the voxel included in the first mask.

5. The method of claim 4, wherein the certain criteria comprises a ratio of lipid included in the voxel to a maximum amount of lipid allowed in the voxel.

6. The method of claim 4, wherein the obtaining the first lipid data further comprises reconfiguring the first lipid data for the voxel included in the first mask by a singular value decomposition (SVD) process.

7. The method of claim 6, wherein the obtaining the metabolite data comprises:

setting a second mask including a voxel having an amount of metabolite greater than that of lipid; and obtaining a spectrum of the voxel having the amount of metabolite greater than that of lipid as the metabolite data.

8. The method of claim 7, wherein the obtaining the metabolite data further comprises reconfiguring the metabolite data by the SVD process.

9. The method of claim 8, wherein the obtaining the metabolite data further comprises:

extracting a spectrum having a maximum peak value among spectrums of the reconfigured metabolite data; and determining the extracted spectrum as the metabolite data.

10. The method of claim 9, wherein the obtaining the second lipid data comprises:

determining correlation of the reconfigured metabolite data and the reconfigured first lipid data;

selecting the reconfigured first lipid data for the voxel included in the first mask based on a predetermined value and the determined correlation; and obtaining the second lipid data by removing the obtained metabolite data from the selected reconfigured first lipid data for the voxel included in the first mask.

11. The method of claim 10, wherein the predetermined value is determined based on at least one among a ratio of lipid included in the obtained metabolite data and a loss rate of the obtained metabolite data comprised of the obtained spectrum data of the voxels of the MR image.

12. The method of claim 10, wherein the estimating the lipid-related spectrum comprises estimating the lipid-related spectrum by projecting the spectrum data of the voxels of the MR image to the obtained second lipid data.

13. The method of claim 12, wherein the removing the estimated lipid-related spectrum comprises removing the estimated lipid-related spectrum from the obtained spectrum data of the voxels of the MR image.

14. The method of claim 1, wherein the obtaining the first lipid data comprises obtaining the first lipid data to include spectrum data of a voxel in which an amount of lipid exceeds a certain criteria, and the obtaining the metabolite data comprises obtaining the metabolite data to include spectrum data of a voxel in which an amount of metabolite is greater than that of the lipid.

15. An apparatus for removing distortion by lipids from a magnetic resonance (MR) image, the apparatus comprising:

a processor configured to obtain an MR image including voxels, obtain data of the voxels from the obtained MR image, obtain a first lipid data based on the obtained data of the voxels, obtain a metabolite data based on the obtained data of the voxels, obtain a second lipid data by removing the obtained metabolite data from the first lipid data, estimate a lipid-related spectrum by using the second lipid data from which the metabolite data has been removed, and remove the estimated lipid-related spectrum from the obtained data of the voxels.

16. The apparatus of claim 15, wherein the processor is configured to obtain spectrum data of the voxels, and generate a map indicating an amount of metabolite and a map indicating an amount of lipid included in the voxels based on the obtained spectrum data.

17. The apparatus of claim 16, wherein the first lipid data is obtained by using the map indicating the amount of the lipid, the metabolite data is obtained by using the map indicating the amount of the metabolite, and the processor is configured to estimate the lipid-related spectrum based on the obtained spectrum data of the voxels from the obtained MR image and the obtained second lipid data.

18. The apparatus of claim 17, wherein the processor is configured to set a first mask including a voxel satisfying a certain criteria in the map indicating the amount of the lipid, and obtain a spectrum of the voxel included in the first mask as the first lipid data for the voxel included in the first mask.

19. The apparatus of claim 18, wherein the certain criteria comprises a ratio of lipid included in a voxel to a maximum amount of lipid allowed in the voxel.

20. The apparatus of claim 18, wherein the processor is further configured to reconfigure the first lipid data for the voxel included in the first mask by a singular value decomposition (SVD) process.

21. The apparatus of claim 20, wherein the processor is configured to set a second mask including at a voxel having an amount of metabolite larger than that of lipid, and obtain a spectrum of the voxel having the amount of metabolite larger than that of lipid as metabolite data.

22. The apparatus of claim 21, wherein the processor is further configured to reconfigure the metabolite data by the SVD process.

23. The apparatus of claim 22, wherein the processor is configured to extract a spectrum having a maximum peak value among spectrums of the reconfigured metabolite data, and determine the extracted spectrum as the metabolite data.

24. The apparatus of claim 23, wherein the processor is configured to determine correlation of the reconfigured metabolite data and the reconfigured first lipid data, select the reconfigured first lipid data for the voxel included in the first mask based on a predetermined value and the determined correlation, and obtain the second lipid data by removing the obtained metabolite data from the selected reconfigured first lipid data for the voxel included in the first mask.

25. The apparatus of claim 24, wherein the processor is configured to determine the predetermined value based on an external input,
  wherein the predetermined value is determined based on at least one among a ratio of lipid included in the obtained metabolite data and a loss rate of the obtained metabolite data comprised of the obtained spectrum data of the voxels of the MR image.

26. The apparatus of claim 24, wherein the processor is configured to estimate the lipid-related spectrum by projecting the spectrum data of the voxels of the MR image to the obtained second lipid data.

27. The apparatus of claim 26, wherein the processor is configured to remove the estimated lipid-related spectrum from the obtained spectrum data of the voxels of the MR image.

28. A non-transitory computer-readable storage medium storing thereon a program, which when executed by a computer, causes the computer to perform the method of claim 1.

* * * * *